United States Patent [19]

Doornbos et al.

[11] Patent Number: 4,889,736
[45] Date of Patent: Dec. 26, 1989

[54] USE OF DIKETONE PRECURSORS IN FOOD PRODUCTS

[75] Inventors: Tamme S. M. Doornbos, Krimpen a/d IJssel; Petrus Haring, Vlaardingen; Arnoldus Van Der Heijden, 's-Gravenzande, all of Netherlands

[73] Assignee: Lever Brothers Company, New York, N.Y.

[21] Appl. No.: 192,733

[22] Filed: May 10, 1988

[30] Foreign Application Priority Data

May 14, 1987 [NL] Netherlands ................ 8701154

[51] Int. Cl.$^4$ ............................................. A23L 1/226
[52] U.S. Cl. .................................. 426/536; 426/534
[58] Field of Search ........................... 426/536, 538

[56] References Cited

U.S. PATENT DOCUMENTS

| 3,887,589 | 6/1975 | Eykelboom et al. ............ 260/347.8 |
| 4,395,430 | 7/1983 | Byrne et al. ........................ 426/534 |
| 4,701,335 | 10/1987 | Doornbos et al. ................ 426/533 |

FOREIGN PATENT DOCUMENTS

| 68774 | 5/1983 | European Pat. Off. . |
| 7309647 | 1/1974 | Netherlands . |
| 1434194 | 5/1976 | United Kingdom . |

OTHER PUBLICATIONS

Shapiro et al., A New Self-Condensation Product of Biacetyl, 1966 Journal of Organic Chemistry pp. 2710-2712.

"Berichte der Deutschen Chemischen Gesellschaft", 21 (1888), 1411 and 1421, by H. von Pechmann (includes translation).

"J. Org. Chem.", 31, (1966), 2710, by Shapiro, Hachmann and Wahl.

"Tetrahedron Letters", 14 (1972), 1307 by J. Kelder and H. Cerfontain.

Primary Examiner—Donald E. Czaja
Assistant Examiner—Evan Federman
Attorney, Agent, or Firm—Milton L. Honig

[57] ABSTRACT

The present invention is concerned with a flavor concentrate containing a precursor of biacetyl, which concentrate is characterized in that it contains 0.1–99 wt. % precursor compound(s) having the following structural formula:

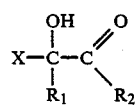

in which X is

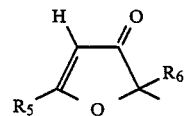

and in which $R_1$, $R_2$, $R_5$ and $R_6$ can differ from each other or can be identical and consist of a methyl or ethyl group.

It has been found that the present precursor compounds release biacetyl upon heating. By using the present precursor compounds in food products problems attached to the use of very volatile diketones in food products may be overcome.

11 Claims, 1 Drawing Sheet

USE OF DIKETONE PRECURSORS IN FOOD PRODUCTS

BACKGROUND OF THE INVENTION

1. Field of the Invention

The present application relates to a flavour concentrate containing a diketone precursor.

2. Prior Disclosures

By diketone precursors are understood compounds that are converted under certain conditions, upon which conversion a diketone is formed. Diketones such as, for instance, biacetyl (2,3-butanedione) and 2,3-pentanedione are compounds which are commonly used for flavouring food products. Thus, biacetyl and 2,3-pentanedione are, for instance, added to margarines to give these products a butter-like flavour. In this application, by the term flavour both the smell and the taste impression are meant.

It has been found that during storage of diketone-containing food products the content of these compounds may decrease drastically with time, probably due to volatilization and/or reaction with other food components and/or oxidation. Besides, it has been found that, upon heating such diketone-containing food products, the diketones volatilize very rapidly, which volatilization is accompanied by the development of an unpleasant, penetrating smell. Moreover as a result of this rapid volatilization the flavour derived from the diketones, during heating, may disappear entirely.

The use of diketone precursors for flavouring food products has already been described in European patent specification EP-C 0 068 774 (Hercules Inc.). This patent specification describes diketone precursors (alpha-ketodiacyloxy compounds) which meet the following structural formula:

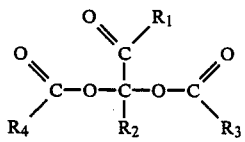

in which $R_1$ and $R_2$ are $C_1$ to $C_5$ hydrocarbon radicals having a total carbon number of 2 to 10, or phenyl radicals, and $R_3$ and $R_4$ are $C_1$ to $C_{18}$ alkyl, cycloalkyl, alkenyl or aryl groups and $R_1$ and $R_2$, or $R_3$ and $R_4$, can be different groups.

In the European patent specification it is reported that, upon heating, these compounds are converted into a diketone and a carboxylic acid. The formation of a carboxylic acid is a disadvantage of the use of these precursor compounds as the formation of said compound may, for instance, adversely affect the pH of the food product, and moreover also its taste and stability.

Dutch patent application NL-A-7309647 (Unilever N.V.) describes the stabilization of dialkyl furenidones, which, in food products, upon storage and heating appear to be unstable, by converting them into corresponding addition products with ketones or aldehydes. These addition products are particularly suitable for addition to food products which are heated to temperatures above 100° C. as they disintegrate on heating, releasing the free furenidone. In Example XII of this application, it is described how the addition product of a dialkyl furenidone and the flavour compound 4-cis-heptenal can be obtained, after which it is stated in Example XV that a frying fat containing this addition product acquires a butter-like character after heating to 150° C.

SUMMARY OF THE INVENTION

It has now been found, that the problem of the decrease of the diketone content in food products, for example upon heating or storage, can be overcome by using a flavour concentrate, which concentrate is characterized in that it contains 0.1–99 wt. %, preferably 1–85 wt. %, precursor compound(s) of the following structural formula:

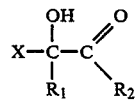

in which X is

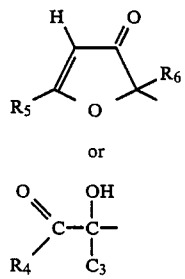

and in which $R_1$, $R_2$, $R_3$, $R_4$, $R_5$ and $R_6$ are different or identical and consist of a methyl or ethyl group.

By flavour concentrate is understood: a composition containing a compound and/or a precursor thereof, which compound is suitable and intended for flavouring food products. Such a composition may be either a liquid or a solid, for example a spray-dried product in which flavour components can be present at a relatively high concentration level.

DETAILED DESCRIPTION OF THE INVENTION

Figure 1:
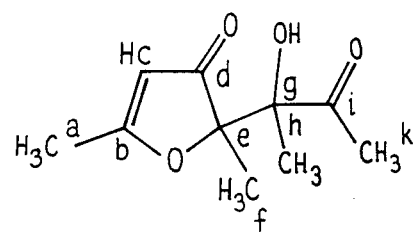

The compound having the structural formula:

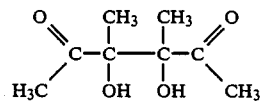

is known from a publication by J. Kelder and H. Cerfontain in Tetrahedron Letters, 14 (1972), 1307, in which it is described how dimers of 1,2-diketones can be obtained by radiation of solutions of 1,2-diketones in 2-propanol with the aid of a vapour lamp with 435 nm as the most intensive line. In this publication it is also reported that the dimer having the above-mentioned structural formula under pyrolysis conditions, i.e. for some hours at 150° C. under nitrogen, is converted into biacetyl and 3-hydroxy-2-butanone.

Furthermore, the dimer of the above-mentioned structure has already been described by H. von Pechmann in Berichte der Deutschen Chemischen Gesellschaft 21 (1888), 1411. On page 1421 a process for preparing the compound is described: zinc powder is added to an aqueous biacetyl solution acidified with diluted sulphuric acid until the solution is colourless and gas is generated. Then, extraction with ether is carried out a few times, after which—after evaporation of the ether—colourless, liquid-soaked crystals are left, which, after recrystallization from ligroin, form long, transparent crystals which melt at 96° C.

The compound of the structural formula:

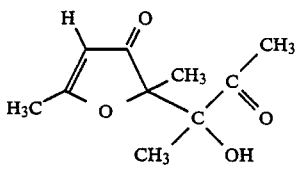

is described by R. Shapiro, H. Hachmann and R. Wahl in *J. Org. Chem.*, 31 (1966), 2710. In this publication it is stated that this compound can be obtained by subjecting biacetyl to a self-condensation reaction in a 0.2% acetic acid solution, by heating such a solution for 13 days at 70° C. In this article it is also reported that this compound disintegrates in strongly alkaline solution, after which—after neutralization—biacetyl can be distilled from the complex reaction mixture.

Since the stability of the present precursor compounds may negatively be affected by the presence of water, the present flavour concentrate preferably comprises less than 20 wt. %, more preferably less than 10 wt. % of water. The flavour-concentrate according to the invention, moreover, preferably comprises less than 95 wt. % of the present precursor compound(s) and at least 5 wt. % of a non-aqueous solid or fluid carrier material.

It was found that the introduction of the present precursor compound(s) into several types of food products, such as for example spreads and cake mixes, is facilitated if said compounds have been spray-dried together with a, preferably water-soluble, carrier material, like skim milk powder and whey powder, under relatively mild conditions. The flavour concentrate thus obtained normally comprises less than 10 wt. % of water and more than 40 wt. % of carrier material. Although the use of dairy powders is preferred also other carrier materials such as salts and natural gums, e.g. maltodextrin may be applied.

Another aspect of the present invention is the use of the present precursor compound(s) for flavouring food products. Preferably said precursor compound(s) are added to the food product at a concentration level of at least 1 ppm, more preferably at a concentration level ranging from 3-100 ppm.

Flavouring of food products can be carried out in a manner known per se by, for example, distributing a flavour concentrate containing one or more compounds according to the present invention homogeneously through the food product. If water-in-oil emulsions like, for instance, margarine are to be flavoured, a flavour concentrate according to the present invention may be added to the fat phase before it is processed with the fatty phase into a water-in-oil emulsion by means of, for instance, a surface-scraped heat exchanger. The words "fat" and "oil" are deemed to be synonymous and therefore used interchangeably throughout this application. By oils and fats are understood not only triglyceride oils but also non-toxic material having physical properties that are comparable with those of triglycerides, which material may partially or completely indigestible such as, for instance, jojoba oil, or poly fatty acid esters of mono- and disaccharides or mixtures of various materials.

Still another aspect of the present invention is a food product containing 1–300 ppm. (mg.kg$^{-1}$), preferably 3–100 ppm (mg.kg$^{-1}$), of the precursor compound(s) according to the present invention. In this application by food product is understood an edible product which, optionally after addition to another edible material, is either suitable for direct consumption or should first be subjected to a heat treatment to make it suitable for consumption.

The concentrations used vary widely depending on the nature of the food product. For instance, in biscuit dough preferably a high concentration of precursor compounds is used because, upon baking with such a dough, a high rate of conversion of the precursor compounds is observed and the compounds formed during the conversion volatilize extremely rapidly. Despite the fact that the conversion compensates the loss of flavour compounds, it is advisable to use an extra high concentration of precursor compounds to prevent the baked biscuits from having too little flavour derived from furanone and/or biacetyl.

Preferably, with the process and in the food product according to the present application, compounds are used in the flavour concentrate in which $R_1$ and $R_2$ are different or identical and together have no more than three carbon atoms, and $R_3$ and $R_4$ are different or identical and together also have no more than three carbon atoms. However, most preferred are the biacetyl precursor compounds in which $R_1$, $R_2$, $R_3$ and $R_4$ are methyl groups. Besides, preferably compounds are used in which $R_5$ and $R_6$ are a methyl group.

A surprising advantage of using a diketone precursor according to the present invention is that, upon heating food products containing such a precursor, under conditions normally encountered in the kitchen, diketone is formed gradually. As a result of the gradual formation of diketone during, for instance, baking, frying or adding hot water to such food products, a flavour inherent to the diketone is released in a controlled manner for a considerable period of time. As the diketone is formed slowly, this flavour release takes longer than when, instead, the food product would have contained an equal amount of free diketone In this manner, baked or fried products can be obtained that still have a diketone flavour (and/or furanone flavour) which is derived almost entirely from diketones formed from the diketone precursors according to the present invention.

Another advantage of the use of diketone precursors according to the invention is that, because of their relatively high stability, when compared to biacetyl, they are suitable for incorporation in food products which, during production or further processing, are subjected to conditions promoting the volatilization of diketone, resulting in a substantial loss of flavour. Thus it is beneficial, inter alia, to incorporate diketone precursors according to the invention in, for instance, spray-dried cake mixes or margarines prepared on a surface-scraped heat exchanger.

It has been found that in case the present precursor compounds are used in, for instance, margarine, small amounts of diketone are formed during storage. As, on storage of a margarine containing these compounds, the very volatile diketone compounds diffuse out of the product, it is advantageous to use precursors of these compounds which, on storage, are converted into free diketone. In this manner, a more efficient flavouring is obtained and, moreover, it is thus accomplished that the products, as the consumer normally buys them after a number of weeks' storage, contain both free ketone compounds and precursor compounds. Such a product has, therefore, a "cold" and a "warm" flavour so that, both when used as, for instance, spread and upon baking and frying with such a product, a pleasant diketone flavour is perceived.

The release of diketone from the present precursor compounds in food products upon storage is in particular observed in food products comprising an aqueous phase, preferably constituting at least 5 wt. % of the product, having a PH of less than 7, more preferably between 4 and 6.

Still another advantage of the use of the compounds according to the present invention as diketone precursors is that, upon heating, these compounds disintegrate into flavour compounds without further byproducts. Such by-products that have no (positive) flavour contribution can, for instance, be formed in the case of flavour compounds which have been stabilized by means of an odourless and tasteless addition group, which groups, possibly through interaction with other food products, might turn out to be bad for the health.

This drawback of by-products does not apply for the diketone dimers which according to the present invention can be used as diketone precursor. On heating, these dimers only give diketone without undesirable by-products.

On heating, the furanone compounds as described above disintegrate into a diketone and 2,5-dialkyl-2,3-dihydrofurane-3-one. This latter compound has been used for quite some time as flavour compound in food products. As the flavour of this furanone complements that of the diketones very well, using precursor compounds from which these compounds are formed, has, on the one hand, the advantage that, during production, these food products do not quickly lose diketone and/or 2,5-dialkyl-2,3-dihydrofurane-3-one and, on the other hand, that on heating two flavour compounds that complement each other are formed without further by-products. Accordingly, the furanone compounds according to the present invention not only act as precursor for diketone but also as precursor for 2,5-dialkyl-2,3-dihydrofurane-3-one.

In addition to the diketone precursors, for the sake of obtaining a more balanced flavour, other flavour compounds and/or precursors thereof may also be used in the present flavour concentrates and food products. Besides the diketone precursors according to the invention, it may be advantageous to additionally incorporate free diketone in food products so that, as long as the food product is not heated, it has a flavour derived from the free diketone and, moreover, upon heating, due to the conversion of precursor compounds, exhibits a diketone flavour during a prolonged period of time.

For the same reason it is also advantageous to incorporate the free furanone compound in the food product. Moreover, it was found that the presence of free diketone and/or furanone compounds enhances the stability of the precursor compounds in the food product or concentrate.

The diketone precursors according to the invention are preferably used in a food product containing 5-99.99 wt. % of fat, 0-95 wt. % of starch and/or starch derivate, 0-90 wt. % of water, wherein fat, starch, starch derivate and water, when taken together, constitute at least 50, preferably at least 80 wt. % of the food product.

In a preferred embodiment of the present invention the food product contains 15-95% fat and 5-85% water, wherein fat and water constitute at least 80 wt. % of the food product. Examples of such a food product are margarines, low calorie spreads, mayonaises, salad dressings and dairy products.

In yet another preferred embodiment of the present invention the food product is a bakery product containing less than 40 wt. % of water, less than 40 wt. % of fat, and at least 40 wt. % of starch and/or starch derivate. Examples of food products containing a starch and/or starch derivate are cake mixes, batters, meal, flour and dough.

By incorporation of biacetyl and/or 2,3-pentanedione precursors, optionally together with several flavour compounds, a butter-like flavour can be imparted to such food products, which is released upon heating and, particularly in case the food product contains an aqueous phase, also during storage. Food products that are particularly suitable are bakery margarine, frying fats and margarines that can be used both as spread and in the kitchen.

The present invention is illustrated by means of the following examples:

EXAMPLE 1

2,5-dimethyl-2-(2-hydroxy-3-oxo-2-butyl)-3(2H)-furanone was prepared as follows:

A mixture of 75.4 g (0.88 mol) redistilled 2,3-butanedione, 750 ml de-ionized water and 1.50 ml acetic acid was stirred for 13 days and heated at a temperature of 65°–71° C. The light-brown solution, which contained a small amount of tar, was filtered to remove the latter. The solution was concentrated under vacuum at a temperature of about 45° C. The remaining volatiles were removed by simultaneous evaporation with toluene (twice 75 ml). The viscous residue (43.8 g) partly crystallized when it was allowed to stand. The product was purified by recrystallizing twice from ether. The mother liquid was removed at about $-40°$ C. and the crystals were subsequently washed at $-25°$ C. with ether and pentane. Yield: 15.1 g colourless crystals, melting point 95°–96° C. (melting point-microscope). Thin-layer-chromatography of the purified product was carried out on $5 \times 10$ cm silicagel 60 $F_{254}$ plates [Merck (trade name)] in the ratio dichloromethane: ether (1:1). Observation under UV or with the aid of iodine vapour only showed one stain.

The isolated product had the following spectra:

Infra-red (KBr): 1688 $cm^{-1}$ and 1715 $cm^{-1}$, C=O stretching vibration; 1610 $cm^{-1}$ C=C ring; 1345$^{-1}$ $CH_3$; 3115 $cm^{-1}$ C—H; 3420 $cm^{-1}$ OH.

NMR (ppm on the low side of the field strength with respect to TMS; $^1H$:360 MHz; $^{13}C$:90.6 MHz; solvent $CDCl_3$) 1.44 (singlet; 3H), 1.48 (singlet; 3H), 2.22 (singlet; 6H), 5.44 (singlet; 1H), 16.76 (singlet; 1C), 17.69 (singlet; 1C), 19.39 (singlet; 1C), 26.10 (singlet; 1C), 81.05 (singlet; 1C), 91.94 (singlet; 1C), 104.46 (singlet; 1C), 189.06 (singlet; 1C), 204.62 (singlet; 1C), 208.66 (singlet, 1C).

EXAMPLE 2

3,4-dihydroxy-3,4-dimethyl-2,5-hexanedione was prepared as follows:

2,3-butanedione (17.0 g; 0.20 mol) was added to a mixture of 60 ml acetic acid and 60 ml de-ionized water.

The solution was cooled in tap water and 30.9 g (0.47 mol) zinc powder was added in small amounts with stirring. During the exothermic reaction a white precipitate formed. The reaction mixture was filtered and the solid material was washed with 75 ml water. The filtrate was concentrated under vacuum at about 20 mm Hg. The semi-solid residue (53 g) was dissolved in 100 ml water and extracted repeatedly (four times) with dichloromethane and once with ether. The combined organic extracts were dried with the aid of anhydrous $Na_2SO_4$ and, after having been filtered, concentrated under vacuum, yielding 7.9 g of a yellowish crystalline material. A pure sample was obtained by two recrystallizations from a mixture of ether and hexane (ratio 1:1) at a temperature of about −25° C. Colourless crystals having a melting point of 94.5°–96° C. (melting point-microscope) were obtained.

The isolated product had the following spectra:

Infra-red: methyl ketone: 2997, 2982, 2942, 2890, 1691, 1462, 1366, 1212 and 1106 $cm^{-1}$ tertiary OH: 3460 and 1144 $cm^{-1}$ NMR (ppm on the side of the low field strength with respect to TMS; $^1H$: 360 MHz; $^{13}C$ 90.6 MHz; solvent $CDCl_3$) 1.28 (singlet, 6H), 2.40 (singlet, 6H), 20.17 (singlet; 2C), 26.38 (singlet; 2C), 81.15 (singlet; 2C), 211.88 (singlet; 2C).

EXAMPLE 3

3,4-dihydroxy-3,4-dimethyl-2,5-hexanedione was prepared by photochemistry. A closed flask [Pyrex (trade mark)], which contained a solution of 20.1 g (0.23 mol) 2.3-butanedione in 81 g 2-propanol, was allowed to stand in daylight for 4.5 months. The solvent was evaporated under reduced pressure (about 20 mm Hg); traces of volatiles were removed by simultaneous evaporation with two parts of toluene of 40 ml. The semi-solid, white residue (13.9 g) was recrystallized twice with a mixture of ether and hexane in a ratio of 1:1, yielding 5.2 g colourless crystals having a melting point of 95°–96° C.

The isolated product showed the same spectra as those that were found for the product mentioned in Example 2.

EXAMPLE 4

The precursor activity of the above compounds was analytically investigated in the temperature ranges that are usually applied for heating food products.

The amount of biacetyl was measured with the aid of a gas chromatograph of the type Perkin Elmer Sigma 300 (trade mark), which was provided with a semi-automatic (headspace) sampler for 6 samples (HS-6) and a 50 M capillary Carbowax column [Chrompack CP52CB (trade mark)] having an internal diameter of 0.32 mm. The stream of nitrogen gas was 1 ml/$min^{-1}$.

Homogeneous solutions of the biacetyl precursor obtained in Example 1 were obtained when 100 mg of this compound was dissolved in 100 ml water or oil. For analysis, 2 g of this solution was poured into a bottle having a volume of 6 ml and a gas-tight closure was mounted on the bottle. The samples were equilibrated for 10 minutes at the temperature indicated before a sample was drawn from the atmosphere above the solution (33 microlitres) and was injected onto the column of the gaschromatograph.

To calculate the amount of biacetyl in the atmosphere above the solution, biacetyl solutions in the same medium were also investigated. Samples of 10, 100 and 500 mg biacetyl/litre water or oil were measured for 10 and 30 minutes after equilibration. No significant differences (about. 5%) were observed between the peak surfaces as these were found after equilibration periods of 10 and 30 minutes. The amounts of biacetyl (mg $l^{-1}$) that were released from the precursor mentioned in Example 1 in water (40° C.; 80° C.) and in oil (120° C.; 150° C.) were determined by the above-mentioned analysis technique, on the basis of the gauge-values found for the biacetyl samples. The data are given in the Table below.

| Medium | | Water | | Oil | |
|---|---|---|---|---|---|
| Temperature (° C.) | | 40° C. | 80° C. | 120° C. | 150° C. |
| Time (in min.) of analyses in the period | 10 min. | 12 | 63 | 12 | 116 |
| after equilibration | 30 min. | 16 | 118 | 25 | 293 |

EXAMPLE 5

The precursor activity of the compound mentioned in Example 2 was measured in the same manner as that described in Example 4. The amounts of released biacetyl (mg.$l^{-1}$) are given in the Table below.

| Medium | | Water | | Oil | |
|---|---|---|---|---|---|
| Temperature (°C.) | | 40° C. | 80° C. | 120° C. | 150° C. |
| Time (in min.) of analyses in the period | 10 min. | 14 | 117 | 80 | 228 |
| after equilibration | 30 min. | 20 | 174 | 119 | 515 |

EXAMPLE 6

The stearin fraction of butter was mixed with the biacetyl precursor mentioned in Example 1, using a scraped-surface heat exchanger, so that the concentration was 50 mg.$kg^{-1}$ and 175 g water per kg of fat. A blank stearin fraction of butter was treated in the same manner without biacetyl precursor being added. Baked products were prepared from these margarines on butter stearin basis, using the following composition:

| |
|---|
| 400 g margarine |
| 500 g flour |
| 75 g milk |
| 5 g baking powder |
| 4 g salt. |

The products were baked for 20 minutes in an oven at a temperature of 190° C. The smell coming from the oven was assessed by an expert panel (14 persons). All panelists stated that, on baking, the products with the biacetyl precursor gave the best butter-like flavour impression. The baked products were subsequently tested by the same panel in groups of two or three samples. Twelve of the fourteen panelists preferred the products with the biacetyl precursor and stated that these products had a more butter-like flavour than the samples without the precursor.

EXAMPLE 7

Margarines were prepared with the aid of a scraped-surface heat exchanger from an aqueous phase (17 wt. %) consisting of (figures based on total product):

skim milk powder (1%)
salt (0.2%)
citric acid (up to pH=5)
potassium sorbate (0.15%)
and partially hydrogenated soybean oil comprising the following components:
Hymono 3203 (trade mark) (0.2%)
beta-carotene (5 ppm)
60 ppm of a commercially available flavour containing butanoic acid, delta-lactones, 4-cis-heptenal, methyl ketones and dimethyl sulphide.

To the margarine was added:
50 ppm of the biacetyl precursor mentioned in Example 2.

A similar blank product was prepared in the same manner, but without the biacetyl precursor.

Samples of margarine were heated to 80° C. and later to 150° C. At these temperatures, the smell above the heated samples was assessed by an expert panel. The panelists stated unanimously that the product containing the biacetyl precursor had a more butter-like smell than the blank sample.

EXAMPLE 8

Rods of puff pastry were prepared from dough consisting of:

| |
|---|
| 500 g flour |
| 250 g water |
| 5 g salt |
| 85 g fat (stearin fraction of butter) |

The dough was kneaded and was allowed to stand for 10 minutes before 340 g fat (stearin fraction of butter) was worked into the fat. A piece of dough was spread out in a rectangle of 10 mm thickness and covered with fat. Subsequently, the spread-out dough was folded, during which the fat was covered and the edges came together. The dough was rolled to a thickness of 10 mm. Subsequently, it was given half a turn and rolled again to 10 mm thickness. The dough was allowed to stand for 40 min., after which the turning and rolling were repeated twice. Finally, the dough was rolled out to a thickness of 1.75 mm and baked in an oven for 20 minutes at a temperature of 220° C.

In the same manner, rods of puff pastry were baked with fat that contained 50 ppm of the biacetyl precursor mentioned in Example 3.

During baking, an expert panel evaluated the smell coming from the ovens and determined that the oven containing the rods of puff pastry with the biacetyl precursor gave a more butter-like and more pleasant flavour than the oven containing the blank rods of puff pastry.

Finally, 12 panelists evaluated the baked rods of puff pastry. Nine panelists stated that the samples containing the precursor had a more butter-like flavour than the blank samples.

EXAMPLE 9

For an aqueous solution containing 0.1 wt. % of the precursor compound prepared in Example 1, it was determined to what extent conversion of the precursor compound into biacetyl and furanone occurred on storage. The solution had a pH of 4.8 and was stored for 9 weeks at 4° C., the content of free biacetyl and furanone being determined by gas chromatography after each week by equilibrating part of the sample at 40° C. as described in Example 4 and drawing a sample of the atmosphere above the solution. It was found that an average of about 3% of the precursor compound per week was converted into biacetyl and furanone. From this it appears that a margarine containing this precursor compound will develop extra flavour on storage, as a result of the conversion of this precursor compound.

EXAMPLE 10

2,5-Dimethyl-2-(2-hydroxy-3-oxo-2-butyl)-3(2H)-furanone were prepared as follows:

A mixture of 98.2 g (1.14 mole) 2,3-butanedione, 700 ml deionized water and 1.50 ml acetic acid was kept at 69°–71° C. in an argon atmosphere for 6 days. The light brown solution containing some tar, was filtered to remove the latter. The solution was continuously extracted with ether for 40 hours. The ethereal extract was dried over anhydrous $Na_2SO_4$, filtered, and the ether evaporated at about 45° C. in vacuo.

The semi-solid residue (76 g) was recrystallized two times from tert. butylmethylether at about −35° C., and subsequently from 100 ml ether at −30° C., giving 26.3 g (yield 35%) of colourless crystals melting at 92.5°–94° C. (melting point microscope using acid-washed cover glasses).

Thin layer chromatography of the recrystallized product was performed with silica F254 plates (ex Merck—Tradename), using a 1:1 mixture of dichloromethane and ether. Detection (UV-light or iodine vapour) showed only one spot.

EXAMPLE 11

A mixture of 30 ml redistilled 2,3-butanedione, 6 ml acetic acid and 64 ml water was stirred and heated at 80° C. for 48 hours, using a reflux condenser. The solution thus obtained was cooled to roomtemperature and extracted with 5 ml dichloromethane. The organic layer was dried over anhydrous sodium sulphate, filtered and concentrated to a syrup under reduced pressure.

The syrup was allowed to stand in a refrigerator. The crystals formed were filtered off and washed with an ether/hexane mixture (1:1 v/v), and subsequently with another ether/hexane mixture (2:1 v/v). The colourless crystals 11A (2.5 g) had a melting point of 83.7° C. (melting point microscope using acid-washed cover glasses; melting point corrected) and the following NMR data:

| | $CDCl_3$ | | $C_6D_6$ | |
|---|---|---|---|---|
| Atom* | $^1$H NMR | $^{13}$C NMR | 1H NMR | $^{13}$C NMR |
| a | 2.24 | 16.92 | 1.50 | 16.10 |
| b | | 190.02 | | 189.53 |
| c | 5.41 | 103.79 | 5.09 | 103.79 |
| d | | 206.06 | | 205.72 |
| e | | 90.57 | | 91.09 |
| f | 1.47 | 17.90 | 1.36 | 17.98 |
| g | | 80.37 | | 80.83 |
| h | 1.47 | 19.44 | 1.42 | 19.57 |
| i | | 209.58 | | 209.31 |
| k | 2.26 | 26.63 | 2.06 | 26.56 |
| OH | 4.16 | | 4.39 | |

*see figure 1

The chemical shifts (in ppm) represented above were obtained at 20° C. for a 10% solution in either $CDCl_3$ or $C_6D_6$. TMS was used as the reference.

The aqueous phases remaining after the first extraction with 5 ml dichloromethane was subsequently three times extracted with 35 ml dichloromethane. The combined organic extracts were dried over anhydrous sodium sulphate, filtered and concentrated to a syrup under reduced pressure.

This syrup was placed in a refrigerator so as to induce crystallization. Crystals formed were filtered off and washed with ether/hexane (1:1; v/v) and ether/hexane (2:3; v/v) mixtures. The white crystals 11B (10 g) thus obtained had a melting point of 92.8° C. (melting point microscope using acid washed cover glasses; melting point corrected). The crystals were dissolved at a concentration level of 10% in CDCl$_3$ and C$_6$D$_6$. NMR data for these solutions were obtained at 20° C., using TMS as the reference. The NMR data obtained were as follows:

| Atom* | CDCl$_3$ | | C$_6$D$_6$ | |
|---|---|---|---|---|
| | $^1$H NMR | $^{13}$C NMR | 1H NMR | $^{13}$C NMR |
| a | 2.22 | 16.76 | 1.45 | 15.91 |
| b | | 189.06 | | 188.57 |
| c | 5.44 | 104.46 | 5.06 | 104.29 |
| d | | 204.62 | | 204.08 |
| e | | 91.94 | | 92.24 |
| f | 1.48 | 17.69 | 1.40 | 17.94 |
| g | | 81.05 | | 81.22 |
| h | 1.44 | 19.39 | 1.36 | 19.42 |
| i | | 208.06 | | 207.95 |
| k | 2.22 | 26.10 | 1.98 | 25.91 |
| OH | 4.10 | | 4.22 | |

*see figure 1

The NMR data represented above show that reaction mixture comprises at least 2 diastereo isomers. It is believed that said mixture in fact comprises 4 diastereo isomers, consisting of two pairs of isomeric compounds which give essentially identical NMR spectra.

The biacetyl release of crystals 11A and 11B was investigated in the same way as described in example 4, by heating water containing 0.1 wt. % of said crystals at 40° and 80° C., and by heating oil containing 0.1 wt. % of said crystals at 80°, 120° and 150° C.

The following results were obtained:

| Medium | 11 A | | | | |
|---|---|---|---|---|---|
| | Water | | Oil | | |
| Temperature (°C.) | 40° C. | 80° C. | 80° C. | 120° C. | 150° C. |
| Time (in min.) of analyses in the period after equilibration | 10 min. | 7 | 65 | 5 | 80 | 310 |
| | 30 min. | 13 | 166 | 14 | 220 | 350 |

| Medium | 11 B | | | | |
|---|---|---|---|---|---|
| | Water | | Oil | | |
| Temperature (°C.) | 40° C. | 80° C. | 80° C. | 120° C. | 150° C. |
| Time (in min.) of analyses in the period after equilibration | 10 min. | * | 29 | 2 | 33 | 158 |
| | 30 min. | * | 74 | 4 | 74 | 343 |

*below detection limit

The results show that both crystals 11A and 11B release substantial amounts of diacetyl upon heating. Crystals 11A, however, appear to more rapidly release diacetyl then crystals 11B in both water and oil, although at 150° C. in fat, after 30 minutes the difference observed was not statistically significant.

We claim:

1. A method for flavouring of food products comprising incorporating within said food products a precursor compound having the following structural formula:

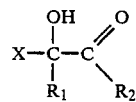

in which X is

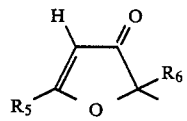

and in which R$_1$, R$_2$, R$_5$ and R$_6$ are different or identical and are selected from ethyl or methyl groups.

2. A method according to claim 1 wherein R$_1$ and R$_2$ are different or identical and together have no more than three carbon atoms.

3. A method according to claim 2 wherein R$_1$, R$_2$, R$_5$ and R$_6$ are methyl groups.

4. Food product containing 1-200 ppm of the precursor compound having the following structural formula:

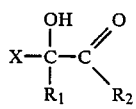

in which X is

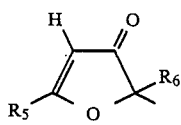

and in which R$_1$, R$_2$, R$_5$ and R$_6$ are different or identical and are selected from ethyl or methyl groups.

5. Food product according to claim 4, wherein the food product contains 3-100 ppm of the precursor compound.

6. Food product according to claim 5, wherein R$_1$ and R$_2$ are different or identical and together have no more than three carbon atoms.

7. Food product according to claim 6, wherein R$_1$, R$_2$, R$_5$ and R$_6$ are methyl groups.

8. Food product according to claim 4, wherein the food product comprises:
   5-99.99 wt. % of fat,
   0-95 wt. % of an ingredient selected from the group consisting of starch, starch derivate, and mixtures thereof,
   0-90 wt. % of water,
   wherein fat, starch, starch derivate and water, when taken together, constitute at least 50 wt. % of the food product.

9. Food product according to claim 8, wherein the food product comprises 15-95% fat and 5-85% water, and wherein fat and water constitute at least 80 wt. % of the food product.

10. Food product according to claim 8, wherein the food product is a mix for baked goods comprising less than 40 wt. % of water, less than 40 wt. % of fat, and at least 40 wt. % of an ingredient selected from the group consisting of starch, starch derivate and mixtures thereof.

11. Food product according to claim 8 wherein fat, starch, starch derivate and water, when taken together, constitute at least 80 wt. % of the food product.

* * * * *